(12) United States Patent
Wang et al.

(10) Patent No.: US 10,379,078 B2
(45) Date of Patent: Aug. 13, 2019

(54) BIOSENSOR AND METHOD FOR ANALYZING ANALYTE CONCENTRATION IN A LIQUID SAMPLE

(71) Applicant: National Tsing Hua University, Hsinchu (TW)

(72) Inventors: Yu-Lin Wang, Zhubei (TW); Jen-Inn Chyi, Zhongli (TW); Chia-Ho Chu, Kaohsiung (TW); Indu Sarangadharan, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 396 days.

(21) Appl. No.: 14/873,765

(22) Filed: Oct. 2, 2015

(65) Prior Publication Data

US 2016/0305900 A1 Oct. 20, 2016

(30) Foreign Application Priority Data

Apr. 20, 2015 (TW) .............................. 104112606 A

(51) Int. Cl.
*G01N 27/327* (2006.01)
*G01N 27/414* (2006.01)

(52) U.S. Cl.
CPC ................................ *G01N 27/4145* (2013.01)

(58) Field of Classification Search
CPC ..... G01N 27/4145; G01N 27/414–417; G01N 27/4167; G01N 27/4117; G01N 27/4035; G01N 27/301; G01N 27/302
See application file for complete search history.

(56) References Cited

U.S. PATENT DOCUMENTS

| | | | |
|---|---|---|---|
| 2007/0074977 A1* | 4/2007 | Guo | A61B 5/14532 205/792 |
| 2007/0095664 A1 | 5/2007 | Chou et al. | |
| 2009/0152127 A1 | 6/2009 | Kaimori et al. | |
| 2011/0068015 A1* | 3/2011 | Park | G01N 27/4145 205/792 |
| 2011/0180856 A1* | 7/2011 | Ahn | G01N 27/4145 257/253 |
| 2014/0054170 A1* | 2/2014 | Tsukahara | G01N 27/327 204/403.01 |
| 2014/0235452 A1* | 8/2014 | Rothberg | G01N 27/4148 506/2 |
| 2016/0169835 A1* | 6/2016 | Sakata | G01N 27/327 204/403.01 |

FOREIGN PATENT DOCUMENTS

TW I279539 B 4/2007
TW I396842 B 5/2013

* cited by examiner

*Primary Examiner* — Gurpreet Kaur
(74) *Attorney, Agent, or Firm* — Birch, Stewart, Kolasch & Birch, LLP

(57) ABSTRACT

A biosensor includes a transistor and a reactive electrode. The transistor has a source, a drain and a gate surface disposed therebetween. The reactive electrode is spaced apart from the gate surface of the transistor, has a receptor immobilized thereon for specific binding with an analyte in a liquid sample, and is configured to contact the liquid sample together with the gate surface of the transistor.

8 Claims, 14 Drawing Sheets

BIOSENSOR AND METHOD FOR ANALYZING ANALYTE CONCENTRATION IN A LIQUID SAMPLE

CROSS-REFERENCE TO RELATED APPLICATION

This application claims priority of Taiwanese Patent Application No. 104112606, filed on Apr. 20, 2015.

FIELD

The disclosure relates to a biosensor, more particularly to a biosensor for analyzing analyte concentration in a liquid sample applied thereto.

BACKGROUND

Referring to FIG. 1, a conventional metal-oxide-semiconductor field effect transistor (MOSFET) biosensor 1 includes a substrate 11, a gate terminal 12, a source terminal 13 and a drain terminal 14. The gate terminal 12, which is formed on the substrate 11, is disposed between the source and drain terminals 13, 14 and has a reactive layer 121 having receptors 15 immobilized thereon for specific binding with an analyte 16 in a liquid sample. By applying the liquid sample onto the reactive layer 121 and applying a bias voltage to the gate terminal 12, a monitored steady-state current obtained from the conventional biosensor 1 can be utilized to detect the analyte concentration in the liquid sample. However, the oxide layer in the conventional MOSFET biosensor may be easily contaminated by the ions in the liquid sample and results in adverse effect on the electrical property thereof. Furthermore, the conventional FET sensors are hard to directly detect analyte in liquid with high ionic strength, such as serum samples, due to a severe charge-screening effect.

SUMMARY

One object of the disclosure is to provide a biosensor which may be easy to fabricate.

According to one aspect of the present disclosure, a biosensor for analyzing concentration of an analyte in a liquid sample applied thereto is provided. The biosensor includes a transistor and a reactive electrode. The transistor has a source, a drain and a gate surface disposed between the source and the drain. The reactive electrode is spaced apart from the gate surface of the transistor and has a receptor immobilized thereon for specific binding with the analyte in the liquid sample. The reactive electrode is configured to contact the liquid sample together with the gate surface of the transistor.

According another aspect of the present disclosure, a method for analyzing concentration of an analyte in a liquid sample may include:

applying the liquid sample to a biosensor, wherein the biosensor includes a transistor that has a drain, a source and a gate surface disposed between the drain and the source, and a reactive electrode spaced apart from the gate surface of the transistor, the reactive electrode having a receptor immobilized thereon for specific binding with the analyte in the liquid sample and being configured to contact with the liquid sample together with the gate surface of the transistor;

applying a voltage pulse between the reactive electrode and the source of the transistor, the voltage pulse having a pulse width;

monitoring a response current, which is produced in response to the voltage pulse within the pulse width from the biosensor; and analyzing the response current that is correlated to the concentration of the analyte in the liquid sample.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
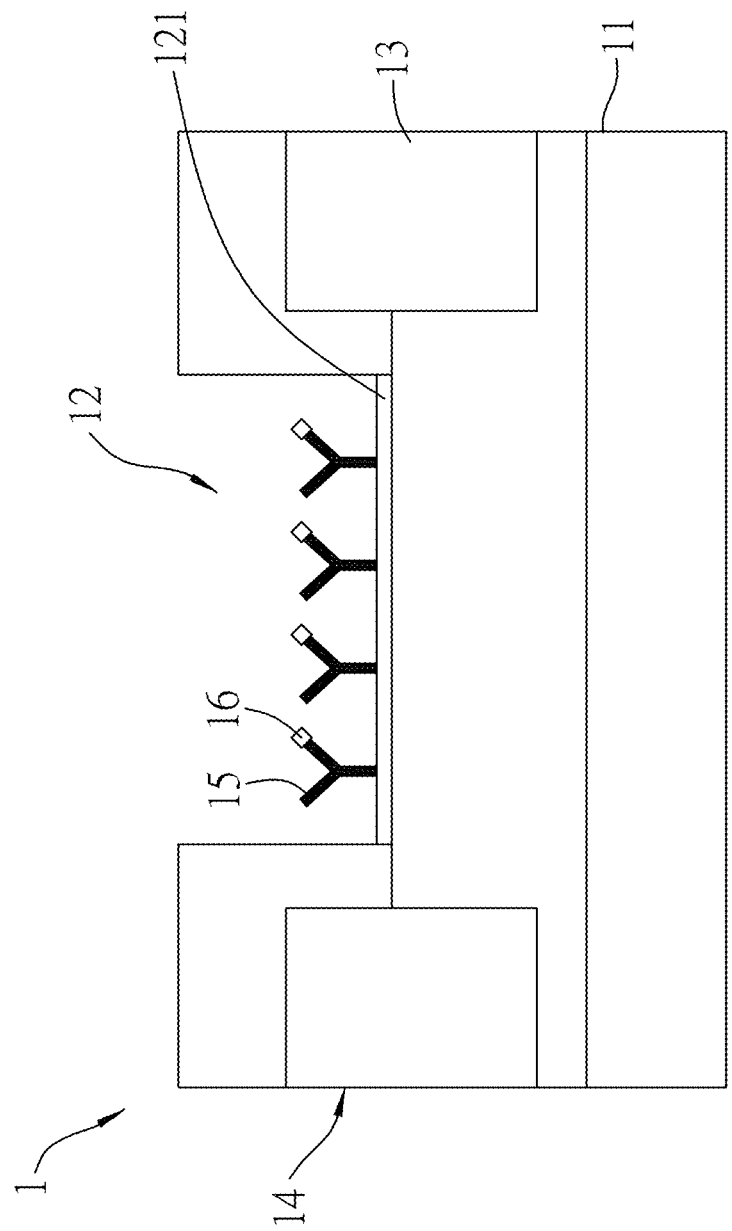
FIG. 1 is a schematic sectional view of a conventional MOSFET biosensor.
Figure 2:
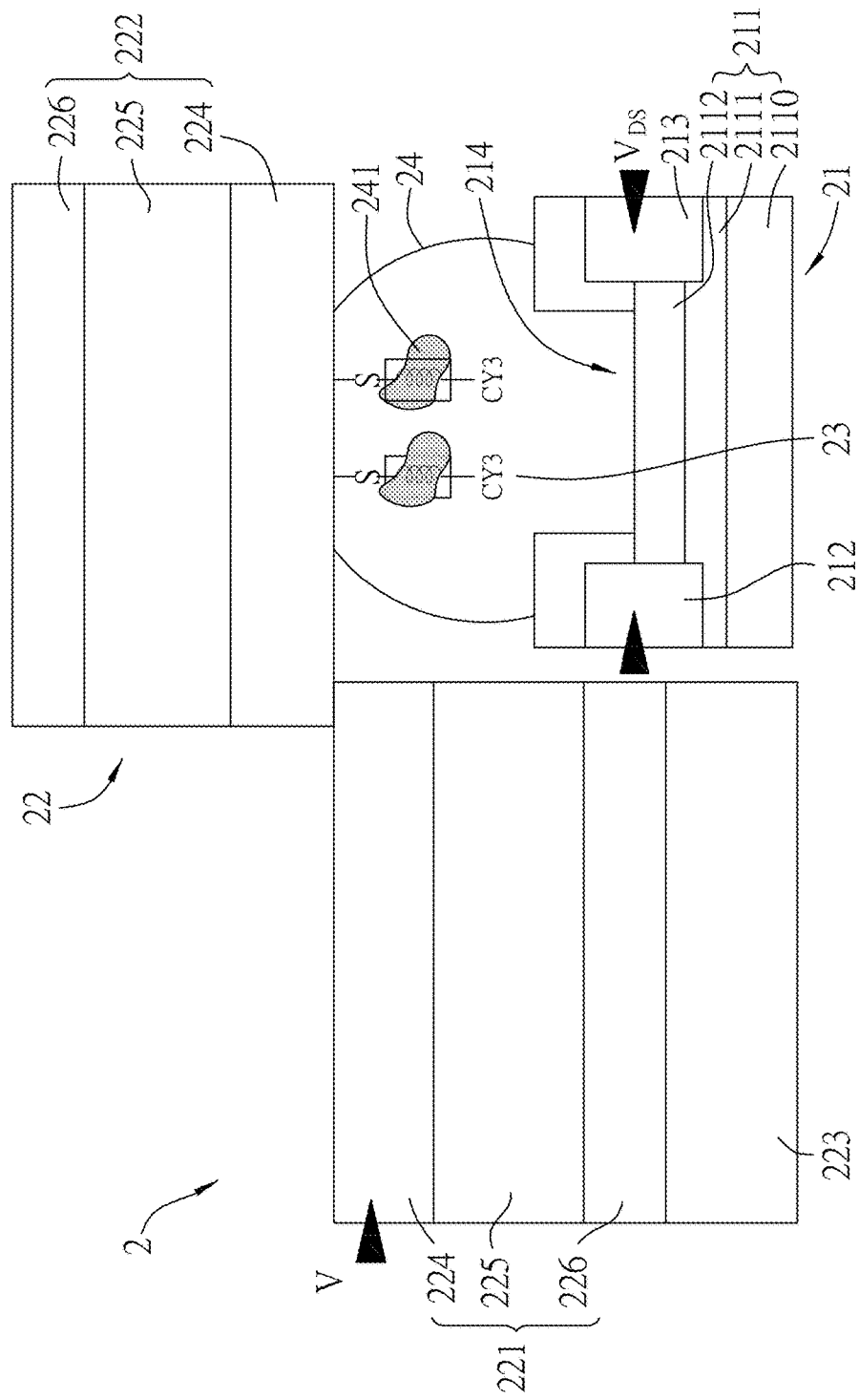
FIG. 2 is a schematic diagram illustrating an exemplary embodiment of a biosensor for analyzing concentration of an analyte in a liquid sample according to the present disclosure.

Referring to FIG. 2, the exemplary embodiment of a biosensor 2 according to the present disclosure for analyzing concentration of an analyte 241 in a liquid sample 24 applied thereto is shown to include a transistor 21 and a reactive electrode 22.

The transistor 21 has a substrate body 211, a source 212 formed on the substrate body 211, a drain 213 formed on the substrate body 211, and a gate surface 214 that is disposed on the substrate body 211 and between the source 212 and the drain 213. The transistor 21 may be selected from the group consisting of a high electron mobility transistor (HEMT), a silicon-based transistor, a nanowire transistor, a graphene transistor, and a molybdenum disulfide ($MoS_2$) transistor. In this embodiment, the transistor 2 is a HEMT and the substrate body 211 thereof includes a sapphire substrate 2110, a gallium nitride (GaN) layer 2111 formed on the sapphire substrate 2110, and an aluminum indium nitride (AlInN) layer 2112 formed on the GaN layer 2111. The HEMT possesses a low-dimensional heterojunction between the AlInN layer 2112 and the GaN layer 2110, so as to greatly enhance carrier transport of the transistor 21. In addition, the GaN layer 2111 is chemically inert and thereby facilitates analyte detection in the liquid sample having relatively high salt concentration. It should be noted that the AlInN layer 2112 of the HEMT may be replaced with other materials, such as aluminum gallium nitride (AlGaN), so long as the heterojunction of the HEMT can be formed between the same and the GaN layer 2111.

The reactive electrode 22 is spaced apart from the transistor 21 and is configured to contact with the liquid sample 24 together with the gate surface 214 of the transistor 21. As shown in FIG. 2, the reactive electrode 22 of this embodiment includes a reactive electrode part 222 disposed on top of the transistor 21 and including a silicon substrate 226, a silicon nitride ($Si_3N_4$) layer 225 that is formed on the silicon substrate 226, and a metal surface layer 224 that is formed on the silicon nitride layer 225 and that faces the gate surface 214 of the transistor 21. The silicon nitride layer 225 serves as a dielectric layer to inhibit electron transport from the metal surface layer 224 to the silicon substrate 211 so as to minimize sensing errors during measurement. In this embodiment, the metal surface layer 224 of the reactive electrode part 222 of the reactive electrode 22 is made of gold, but the metal surface layer 224 may be made of other metals (e.g., platinum), alloys or conductive materials having affinity to biological molecules and thus should not be limited to the disclosure of this embodiment. The metal surface layer 224 of this embodiment may include gold nano-particles, which can be formed by chemical reduction, to further improve biological affinity of the reactive electrode 22. Since the technique of forming the gold nano-particles may be readily appreciated by those skilled in the art, further details will not be provided herein for the sake of brevity.

In this embodiment, as shown in FIG. 2, the reactive electrode 22 further includes an auxiliary electrode part 221 disposed beside the transistor 21. In greater detail, the auxiliary electrode part 221 includes a silicon substrate 226 disposed on a glass substrate 223, a silicon nitride ($Si_3N_4$) layer 225 formed on top of the silicon substrate 226 opposite to the glass substrate 223, and a metal surface layer 224 formed on top of the silicon nitride layer 225 (i.e., having similar configuration as the reactive electrode part 222). The total height of the auxiliary electrode part 221 and the glass substrate 223 is greater than that of the transistor 21. The reactive electrode part 222 has a portion of the metal surface layer 224 physically and electrically contacting the metal surface layer 224 of the auxiliary electrode part 221, while a remaining portion of the metal surface layer 224 faces and is spaced apart from gate surface 214 of the transistor 21. It should be noted that the structure of the reactive electrode part 222 of the reactive electrode 22 may be configured in a different manner in other embodiments (e.g., configured as a single metal piece instead of a multi-layer stacked structure). In addition, the configuration of the auxiliary electrode part 221 of the reactive electrode 22 may be different from that of the reactive electrode part 222 in other embodiments of the present disclosure, so long as the auxiliary electrode part 221 is electrically coupled to the reactive electrode part 222 for signal transmission.

As illustrated in FIG. 2, the metal surface layer 224 of the reactive electrode part 222 has a receptor 23 immobilized thereon for specific binding of the analyte 241. For example, when the analyte 241 is a protein, such as a HIV-1 reverse transcriptase (HIV-1 RT) protein or a carcino-embryonic antigen (CEA), the receptor 23 can include duplex deoxyribonucleic acid (dsDNA) molecules or antibodies which can specifically bind to the analyte 241. It should be noted that there is no other limitation on the selected receptor 23, so long as the receptor 23 can be immobilized on the metal surface layer 224 and facilitate specific binding with the analyte 241. In an embodiment where the metal surface layer 224 of the reactive electrode 22 is immobilized with the receptor 23, the surface of the metal surface layer 224 exposed from the receptor 23 may be blocked using a blocking protein to promote the specific binding between the analyte 241 and the receptor 23 (in other words, to inhibit nonspecific binding of the analyte 241 to the gate surface 214). Such blocking may be conducted using a protein solution. The blocking protein may be, but is not limited to, bovine serum albumin (BSA) or the like.

Figure 3:
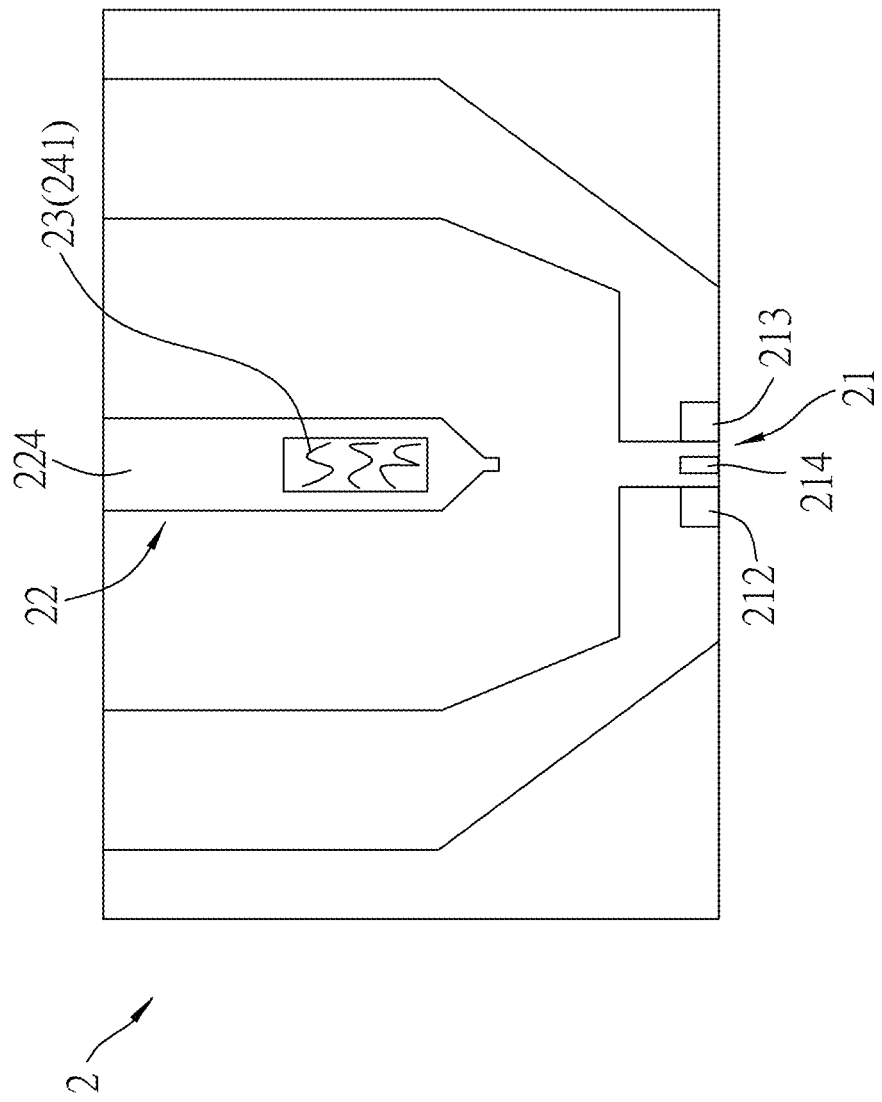
FIG. 3 is a schematic top view of the exemplary embodiment, illustrating a variation of the biosensor.

In a variation of this embodiment, the biosensor 2 may be configured as illustrated in FIG. 3, where the metal surface layer 224 of the reactive electrode 22 and the gate surface 214 of the transistor 21 are arranged in a coplanar manner and the auxiliary electrode part 221 of the reactive electrode 22 is omitted. Moreover, the reactive electrode 22 and the transistor 21 are integrally fabricated as a single piece (i.e., the substrate body 211 of the transistor 21 is extended to allow the reactive electrode 22 to be incorporated thereon). In this modified embodiment, the AlInN layer 2112 of the transistor 21 may be replaced by an aluminum gallium nitride (AlGaN) layer and the transistor 21 may still have similar performance with respect to carrier transport.

A method for utilizing the biosensor 2 of the exemplary embodiment according to the present disclosure includes Steps 200 to 204.

Step 200: applying the liquid sample 24 to the biosensor 2. As illustrated in FIG. 2, the liquid sample 24 containing the analyte 241 is applied into a gap between the metal surface layer 224 of the reactive electrode part 222 of the reactive electrode 22 and the gate surface 214 of the transistor 21 (see FIG. 2). The liquid sample 24 may be, but is not limited to, a buffer solution (e.g., tris-EDTA buffer or phosphate saline buffer) or a biological sample such as human blood, blood serum and blood plasma, etc. It should be noted that, when the liquid sample 24 is a buffer solution, the liquid sample 24 may be added with a reference protein, such as bovine serum albumin, to simulate the characteristics of human serum samples which contain the target analyte 241 together with various background proteins having relatively high concentrations. The analyte 241 in the liquid sample 24 may specifically bind to the receptor 23 after a short period of time, for instance, 5 minutes, depending on the specie thereof.

Step 201: applying a voltage pulse (V) to the liquid sample 24 which is applied to the biosensor 2 (see FIG. 2).

In Step 201 of this embodiment, the voltage pulse (V) is applied between the auxiliary electrode part 221 of the reactive electrode 22 and the transistor 21. The applied voltage pulse (V) has a pulse width that is not greater than $10^{-3}$ second. Within such pulse width, the transient current response of the liquid sample 24 at the biosensor 2 does not reach a steady state. In some embodiments, the pulse width may range from 2 μs to 100 μs. In some embodiments, the pulse width may range from 30 μs to 60 μs. The applied voltage pulse (V) may have an amplitude that is not greater than a redox potential of the receptor 241. In this embodiment, the amplitude of the voltage pulse (V) is about 0.5V. It is worth noting that Step 201 can be conducted by a meter, an analyzer, a voltage generator and the like, and the biosensor 2 of this embodiment may be incorporated into a sensor strip.

It should be noted that, a working voltage ($V_{DS}$) may be applied between the source 212 and the drain 213 of the transistor 21 before the application of the voltage pulse (V), so as to enable the transistor 21 to have amplifying function. The working voltage ($V_{DS}$) may be in a range of 0.5 V to 10 V for enabling linear operation of the transistor 21. Step 202: monitoring a response current within the pulse width of the voltage pulse (V) from the source 212 of the transistor 21 of the biosensor 2. The application of the voltage pulse (V) produces a response current that is in response to the voltage pulse (V) due to the capacitance effect of the liquid sample 24 between the reactive electrode 22 and the gate surface 214 of the transistor 21 and that is amplified by the transistor 21. It should be noted that the response current may be monitored from either source 212 or drain 213 of the transistor using a recorder or an analyzer, such as Agilent B1530A. It should also be noted that, in other embodiments, a response power, a response frequency, a response capacitance or a response impedance, which is in response to the voltage pulse, may be monitored and should not be limited to what is disclosed in this embodiment according to the present disclosure.

Step 203: analyzing the response current that is correlated to the concentration of the analyte 241 in the liquid sample 24. The monitored response current can be analyzed using any suitable means, such as computers, analyzers or the like.

In one variation of this embodiment, when the liquid sample 24 is added with a predetermined amount of the reference proteins, the method may further include a step of performing subtraction processing on the response current to subtract a reference response current contributed by solely the reference proteins provided in the liquid sample 24 from the monitored response currents.

In one variation of this embodiment, the method may further include a step of performing integration computational processing on the response current with respect to at least a certain period in the pulse width in accordance with the following equation:

$$Q = I \times t$$

where a total charge (Q) accumulated on the electrodes 21 within the certain period in the pulse width (t) can be calculated from the response current (I). Such parameter obtained by performing the aforesaid integration computational processing may serve as an alternative or additional analyzing factor for analyzing the concentration of the analyte 241 in the liquid sample 24.

A time constant (τ) may serve as another alternative or additional analyzing factor for analyzing the concentration of the analyte 241 in the liquid sample 24, and is represented by the following equation:

$$\langle \tau \rangle = \int \frac{I(t)}{I_{peak}} dt$$

In other words, in a variation of the exemplary embodiment, the method may further include steps of performing arithmetic computational processing to divide entries of the response current by a maximum value ($I_{peak}$) thereof, and performing integration computational processing on results of the arithmetic computational processing with respect to at least a certain period in the pulse width to obtain the time constant (τ).

By utilizing the reactive electrode 22, the biosensor 2 of the present disclosure is easy to fabricate since immobilization of the receptor 241 on the reactive electrode 22 is relatively simple rather than immobilizing the same on the gate surface 214 of the transistor 21. Moreover, by incorporating the transistor 21 and the reactive electrode 22 into the biosensor 2 of the present disclosure, the response current in response to the analyte concentration due to the capacitance effect between the metal surface layer 224 of the reactive electrode 22 and the gate surface 214 of the transistor 21 may be amplified, so as to further lower the detection limit of the biosensor 2 according to the disclosure. Furthermore, by adopting the aforementioned method of the present disclosure, liquid samples having high salt concentrations can be directly analyzed using the biosensor of the present disclosure without the need of being further diluted, i.e., the so-called charge-screening effect caused by high-concentration salt ions in the liquid sample can be easily avoided.

The following examples are for illustrating the exemplary embodiment only and should not be construed as limiting the scope of the present disclosure.

EXAMPLES

Immobilization of the Receptor

5 μL of a phosphate buffer saline (PBS) solution, with a pH value of 7.4, was applied dropwise to the gap between the reactive electrode 22 and the transistor 21 of the biosensor 2 as illustrated in FIG. 2, so as to allow the metal surface layer 224 together with the gate surface 214 of the transistor 21 contacted the PBS buffer solution. Thereafter, a working voltage ($V_{DS}$) of 0.5 V was applied to the transistor 21 while the source 212 of the transistor 21 was grounded. Thereafter, a voltage pulse (V) having a pulse width of 50 μs and an amplitude of 0.5 V was applied to the reactive electrode part 222 of the reactive electrode 22 via the auxiliary electrode part 221 by an analyzer (Model: B1530/B1500A, commercially available from Agilent). A first response current was measured accordingly from the source 212 of the transistor 21. After removing the PBS buffer solution, 5 μL of 5×10$^{-6}$ M dsDNA solution containing duplex DNA molecules (i.e., the receptor 23) was applied dropwise onto the metal surface layer 224 of the reactive electrode 22 and remained thereon for 24 hours at 25° C., allowing the duplex DNA molecules to be immobilized thereon. The duplex DNA molecules have sequences of 5'-TTT GCT TTT TCG TCG TTT GCT TTT CGT TTT-thiol-3' and 5'-(Cy3)-AAA ACG AAA AGC AAA CGA CGA AAA AGC AAA-3', respectively. Thereafter, the reactive electrode 22 and the transistor 21 were rinsed twice using phosphate buffer (pH=8) to remove non-binding dsDNA molecules. The PBS buffer solution was then applied again to the gap between the reactive electrode 22 and the transistor 21 of the biosensor 2, and the same working voltage and the same voltage pulse was again applied to the biosensor 2, so as to obtain a second response current. By comparing the first and second response currents, immobilization of the duplex DNA molecules on the metal surface layer 224 can be ascertained.

Example 1

Figure 4:
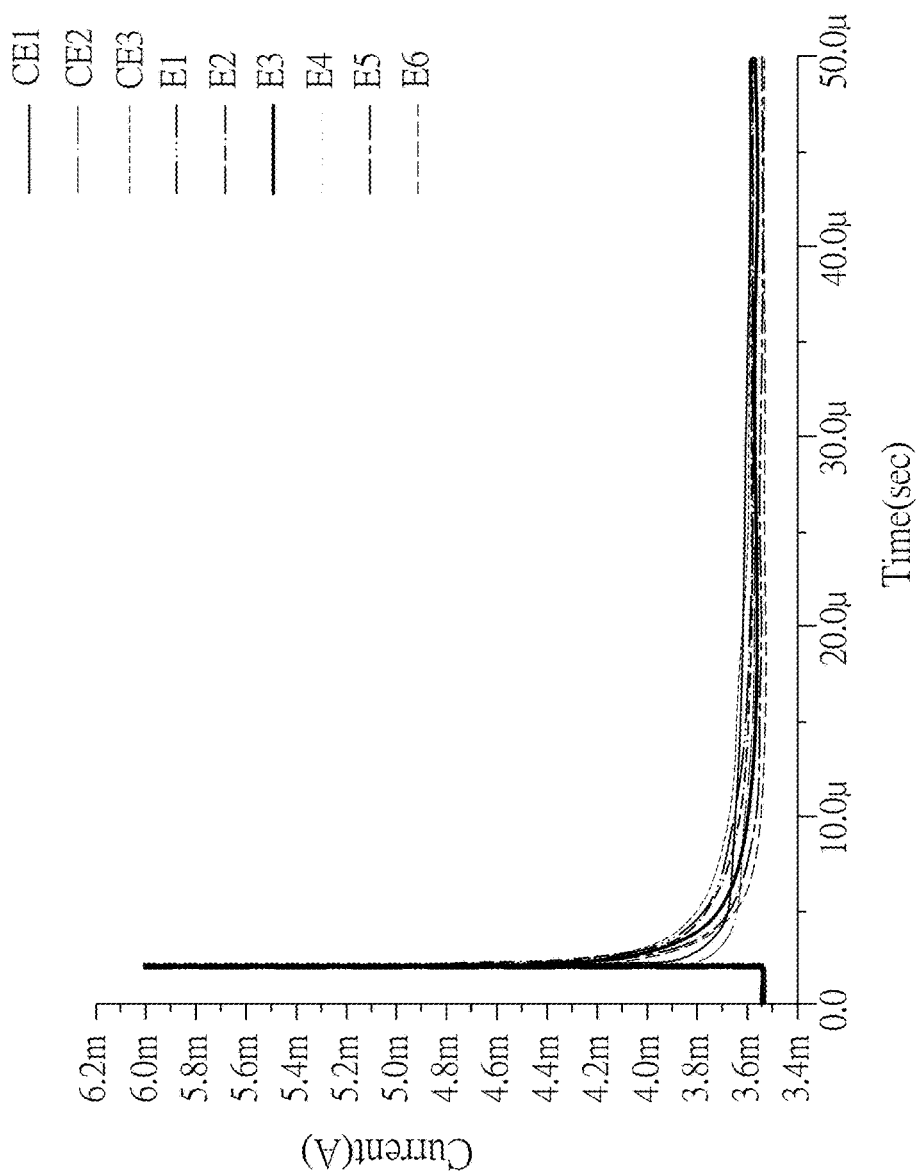
FIG. 4 shows plots of response currents of Examples 1 to 6 and Comparative Examples 1 to 3 with respect to voltage pulse applying time.
Figure 5:
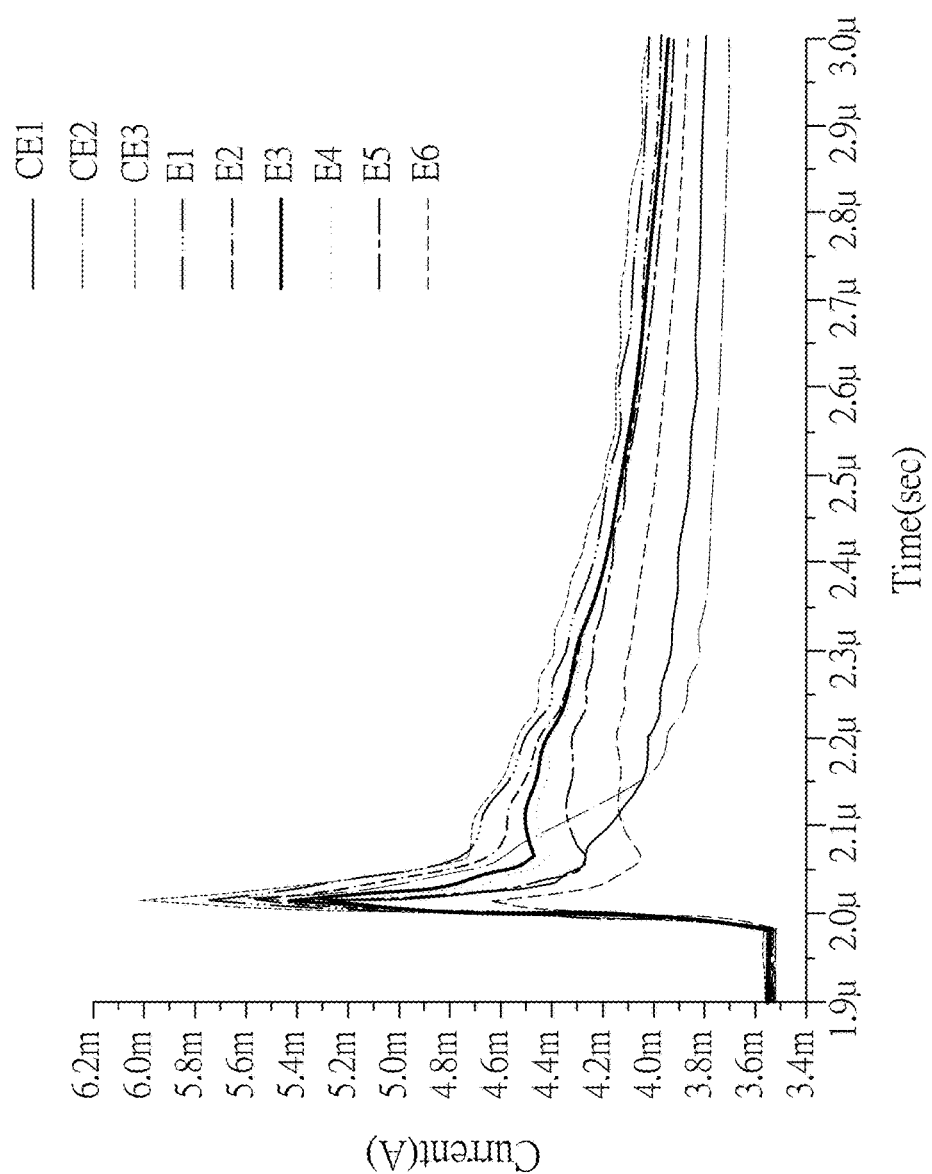
FIG. 5 shows a zoomed-in view of FIG. 4.
Figure 6:
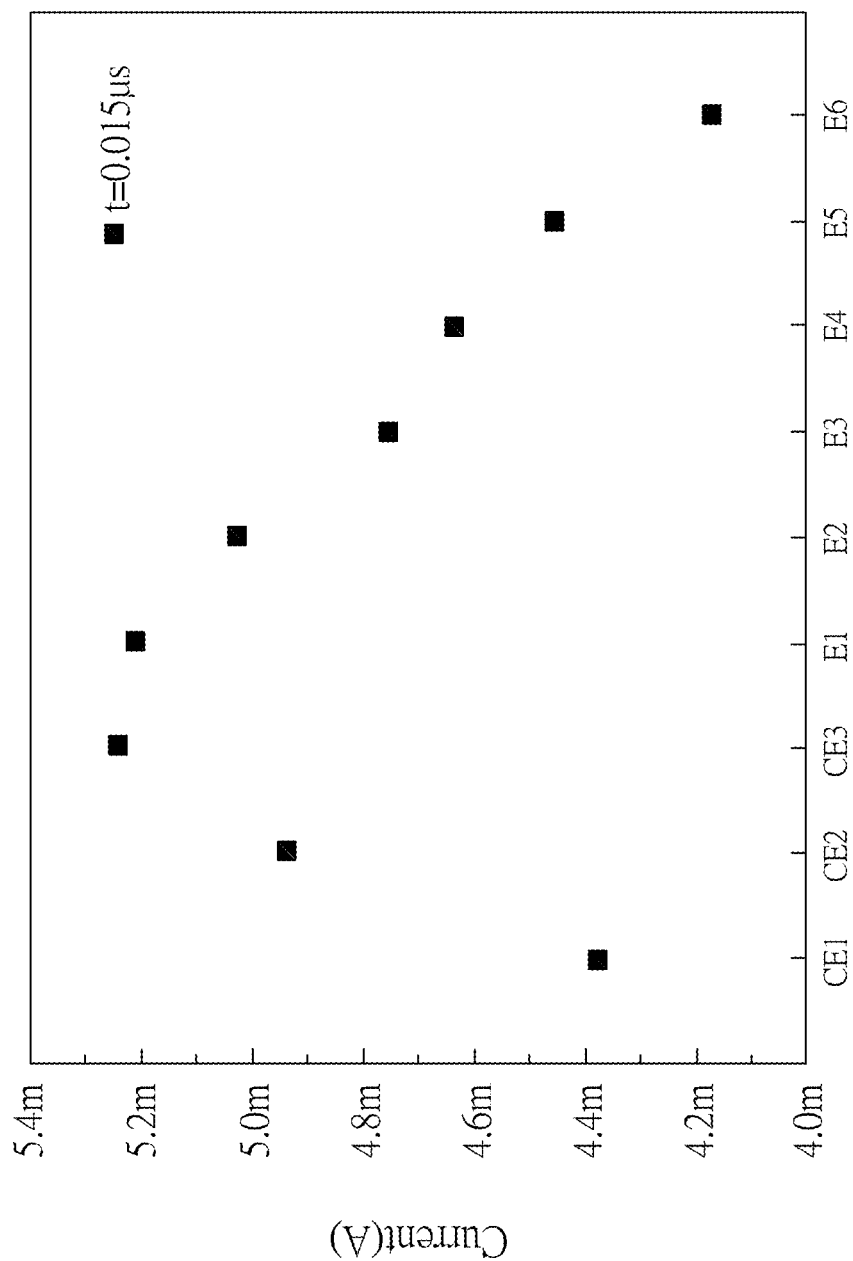
FIG. 6 shows the response currents of Examples 1 to 6 and Comparative Examples 1 to 3 at 0.015 µs after the application of the voltage pulse.

A BSA/PBS buffer solution, containing 4% of BSA and serving as a reference/blocking protein solution, was applied onto the metal surface layer 224 of the reactive electrode 22 to block the surface of the metal surface layer 224 exposed from the immobilized duplex DNA molecules. A working voltage of 0.5V was first applied to the transistor 21 and a voltage pulse having a pulse width of 50 μs and an amplitude of 0.5 V was then applied between the reactive electrode 22 and the transistor 21 by the analyzer (Model: B1530/B1500A, commercially available from Agilent) 2 μs after the application of the working voltage, so as to obtain a reference response current. Subsequently, the BSA/PBS buffer solution was removed using an elution buffer, and 5 μL of a HIV-1 RT protein solution (i.e., the liquid sample 24), containing 4% of BSA and the HIV-1 RT protein (i.e., the analyte 241) at a concentration of 1 aM, was applied to the gap between the metal surface layer 224 of the reactive electrode 22 and the gate surface 214 of the transistor 21 for 5 minutes at 25° C. Thereafter, the same working voltage and the same voltage pulse were again applied to the biosensor 2 by an analyzer (Model: B1530/B1500A, commercially available from Agilent). A response current was monitored and is illustrated in FIGS. 4 to 6.

Examples 2 to 6

The methods of Examples 2 to 6 were similar to that of Example 1, with the sole difference residing in that the liquid samples of Examples 2 to 6 have HIV-1 RT protein concentrations of 10 aM, 1 fM, 10 fM, 100 fM and 1 pM, respectively. The monitored response currents are illustrated in FIGS. 4 to 6.

Example 7

Figure 13:
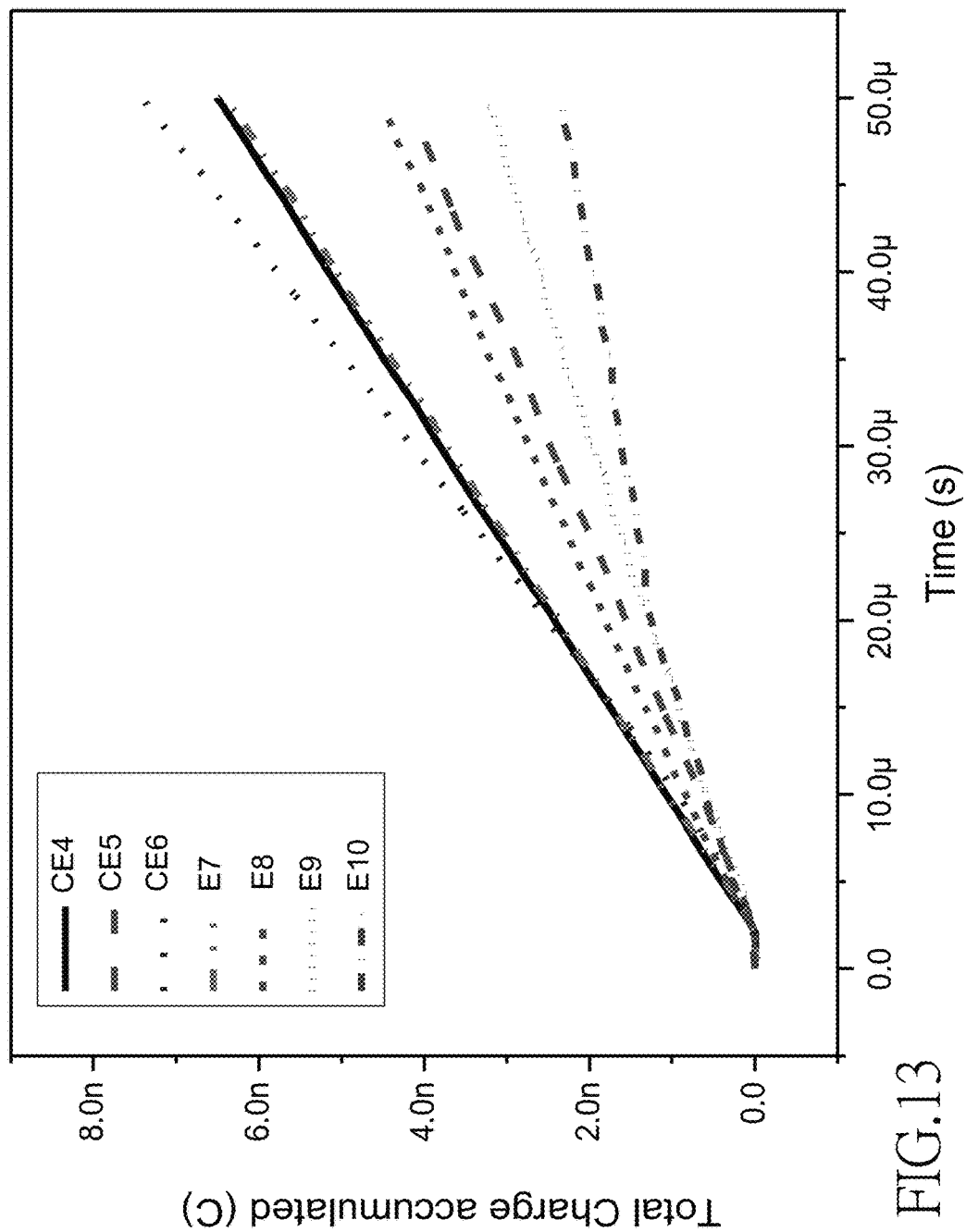
FIG. 13 shows the accumulated total charges of Examples 7 to 10 and Comparative Examples 4 to 6 with respect to the voltage pulse applying time.

The method of Example 7 was similar to that of Example 1, with the differences residing as follows. The biosensor 2 used in this example is configured as illustrated in FIG. 3, where the gate surface 214 of the transistor 21 and the metal surface layer 224 of the reactive electrode 22 are arranged in a coplanar manner. In addition, the liquid sample 24 is a CEA protein solution (i.e., the analyte 241 is a CEA protein), containing 100 fM of CEA protein and 1% of BSA (i.e., the blocking/reference protein). The receptor immobilized on the metal surface layer 224 of the reactive electrode 22 was an anti-CEA antibody, and the working voltage was set to 2V. It should be noted that the native thiol groups in the hinge region of the receptor 23 were utilized to allow binding of the receptor 23 onto the metal surface layer 224 of the reactive electrode 22, so as to facilitate immobilization of the anti-CEA antibody on the reactive electrode 22. The total accumulated charges (Q) of Example 7 calculated by integrating the monitored response current (I) over a voltage applying period (t) is illustrated in FIG. 13.

Examples 8 to 10

The methods of Examples 8 to 10 were similar to that of Example 7, with the sole difference residing in that the liquid samples 24 of Examples 2 to 6 have CEA protein concentrations of 1 pM, 10 pM and 100 pM, respectively. The total accumulated charge calculated from the monitored response currents of Examples 8 to 10 are illustrated in FIG. 13.

Comparative Example 1

The method of Comparative Example 1 was similar to that of Example 1. The differences therebetween reside in that the liquid sample applied to the biosensor in the method of Comparative Example 1 is a 1×PBS buffer solution with no HIV-1 RT protein (i.e., the analyte) contained therein, that no duplex DNA molecules (i.e., the receptor 23) were immobilized on the metal surface layer 224 of the biosensor 2 of Comparative Example 1, and that the metal surface layer 224 of the reactive electrode 22 was not blocked by the BSA protein (i.e., no blocking/reference protein solution was utilized). The monitored response current of Comparative Example 1 is illustrated in FIGS. 4 to 6.

Comparative Example 2

The method of Comparative Example 2 was similar to that of Comparative Example 1, with the only difference residing in that the metal surface layer 224 of the biosensor 2 was immobilized with the DNA duplex molecules (i.e., the receptor 23). The monitored response current of Comparative Example 2 is illustrated in FIGS. 4 to 6.

Comparative Example 3

The method of Comparative Example 3 was similar to that of Comparative Example 2, with only the difference residing in that the liquid sample applied to the biosensor was a PBS/BSA buffer solution having BSA concentration of 4% (i.e., the reference/blocking protein solution) but containing no analytes. The monitored response current of Comparative Example 3 (i.e., the reference response current) is illustrated in FIGS. 4 and 6.

Comparative Example 4

The method of Comparative Example 4 was similar to that of Example 7. The differences therebetween reside in that the liquid sample applied to the biosensor in the method of Comparative Example 4 is 1×PBS buffer solution with no CEA proteins contained therein, that the metal surface layer 224 of the reactive electrode 22 was not blocked by the BSA protein (i.e., no blocking/reference protein solution was utilized) and that no anti-CEA antibody (i.e., the receptor 23) was immobilized. The accumulated total charge calculated from the monitored response current of Comparative Example 4 is illustrated in FIG. 13.

Comparative Example 5

The method of Comparative Example 5 was similar to that of Comparative Example 4, with the only difference residing in that the metal surface layer 224 of the biosensor 2 was immobilized with the anti-CEA antibody (i.e., the receptor 23). The accumulated total charge calculated from the monitored response current of Comparative Example 5 is illustrated in FIG. 13.

Comparative Example 6

The method of Comparative Example 6 was similar to that of Comparative Example 5, with only the difference residing in that the liquid sample applied to the biosensor was a PBS/BSA buffer solution having BSA concentration of 1% (i.e., the reference/blocking protein solution) but containing no analytes. The accumulated total charge calculated from the monitored response current of Comparative Example 6 is illustrated in FIG. 13.

[Data Analysis]

FIGS. 4 to 6 show plots of the response currents of Examples 1 to 6 and Comparative Examples 1 to 3 with respect to the voltage pulse applying time, wherein FIG. 4 shows the response currents of Examples 1 to 6 and Comparative Examples 1 to 3, FIG. 5 is a zoomed-in view of FIG. 4, FIG. 6 shows the response currents at 0.015 µs after the application of the voltage pulse (i.e., 2.015 µs after the application of the working voltage). It is clearly shown that the liquid samples with various analyte concentrations indeed have respective response currents under the same applied voltage pulse and the same working voltage. In addition, with the increasing analyte concentrations in the liquid samples, the response currents of Examples 1 to 6 (see FIG. 6) tend to decrease accordingly.

Figure 7:
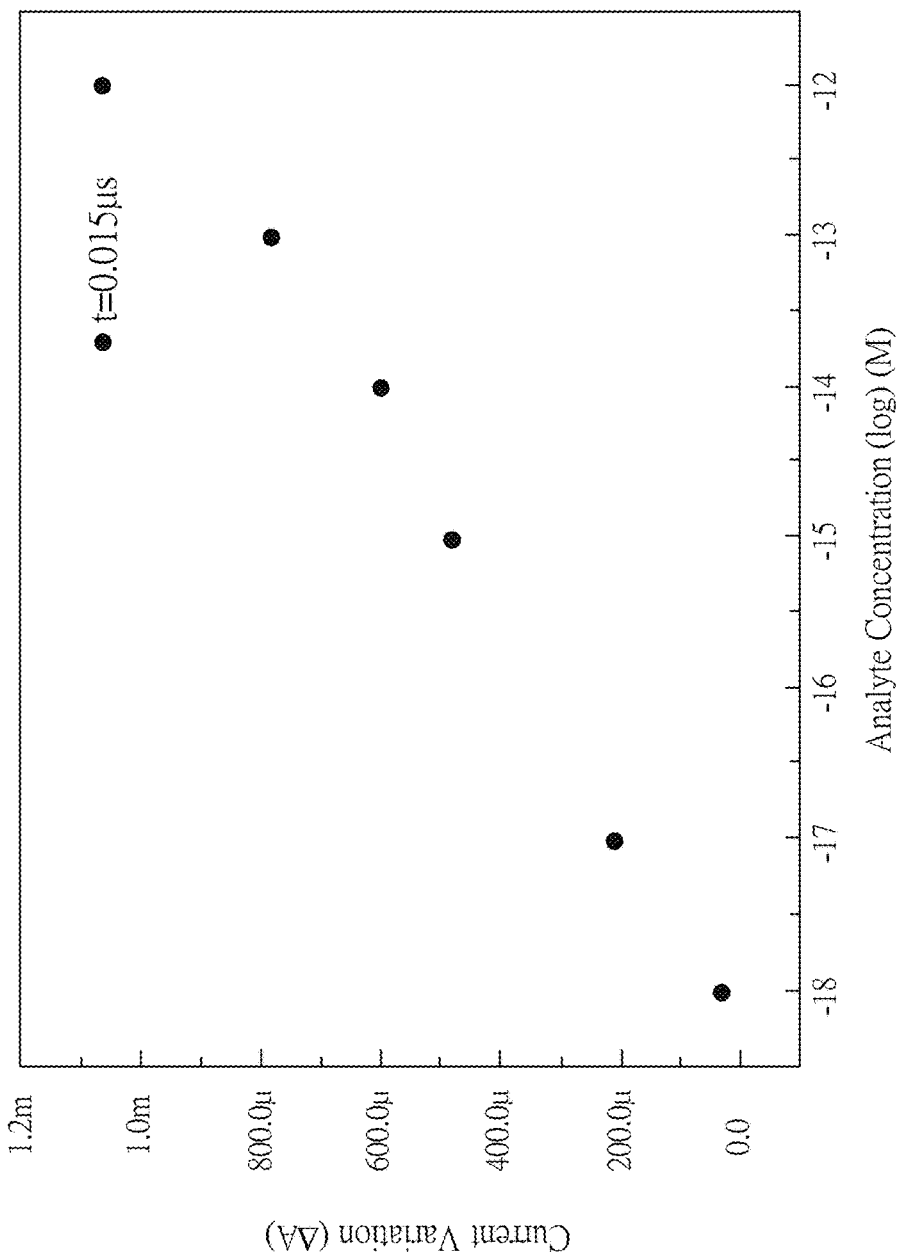
FIG. 7 shows the response current variations between each of Examples 1 to 6 and Comparative Example 3 at 50 µs after the application of the voltage pulse with respect to the analyte concentration in a logarithmic scale.

FIG. 7 shows response current variations between each of Examples 1 to 6 and Comparative Example 3 at 0.015 µs after the application of the voltage pulse, where the subtraction processing was conducted (i.e., to subtract out the reference response current obtained from Comparative Example 3). It further illustrates that the response currents of Examples 1 to 6 are approximately in proportion to the logarithmic analyte concentration in the liquid samples. These results prove that the response current monitored within the pulse width of the voltage pulse is correlated to the analyte concentration in the liquid sample applied to the biosensor and can be utilized as a reliable analyzing factor.

Figure 8:
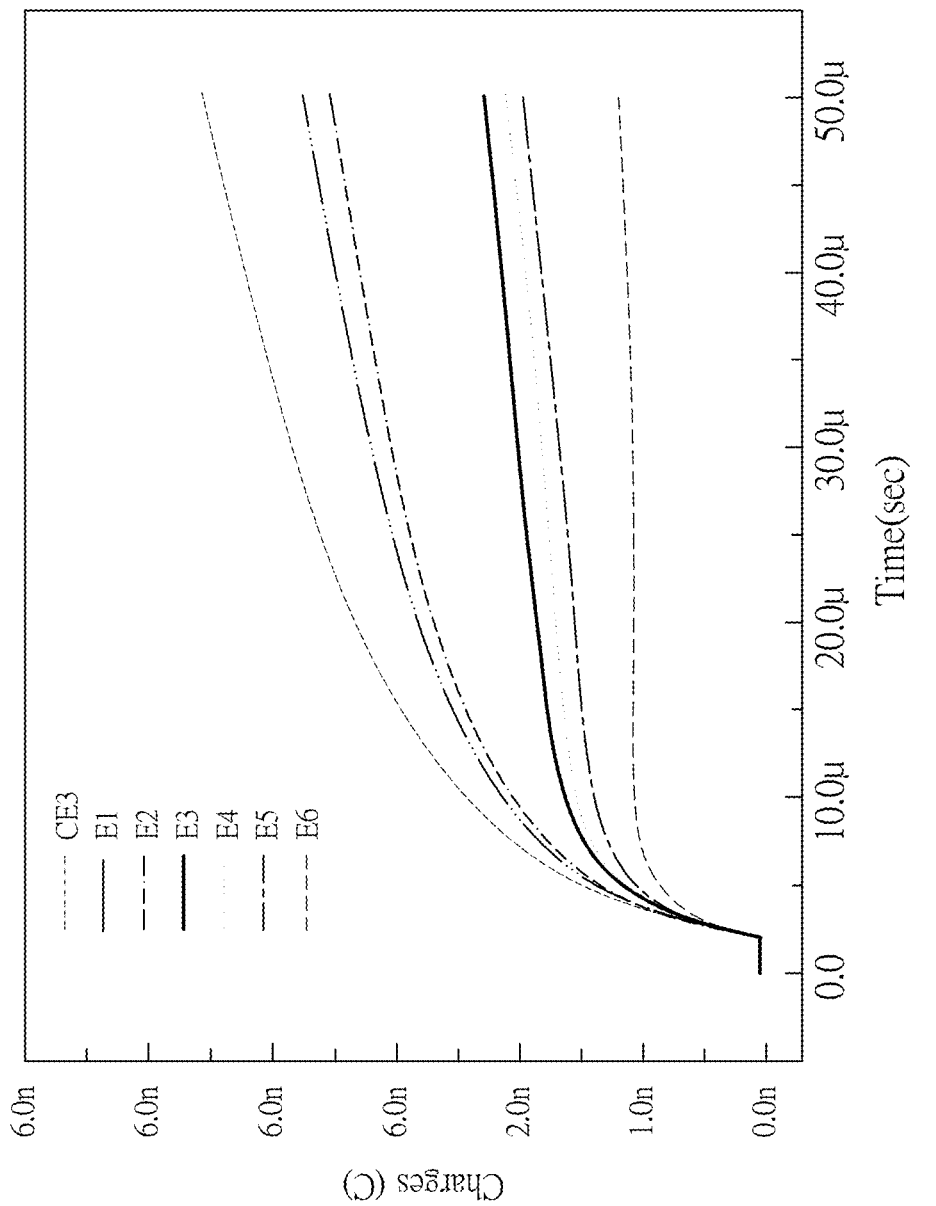
FIG. 8 shows the accumulated charges of Examples 1 to 6 and Comparative Example 3 with respect to the voltage pulse applying time.
Figure 9:
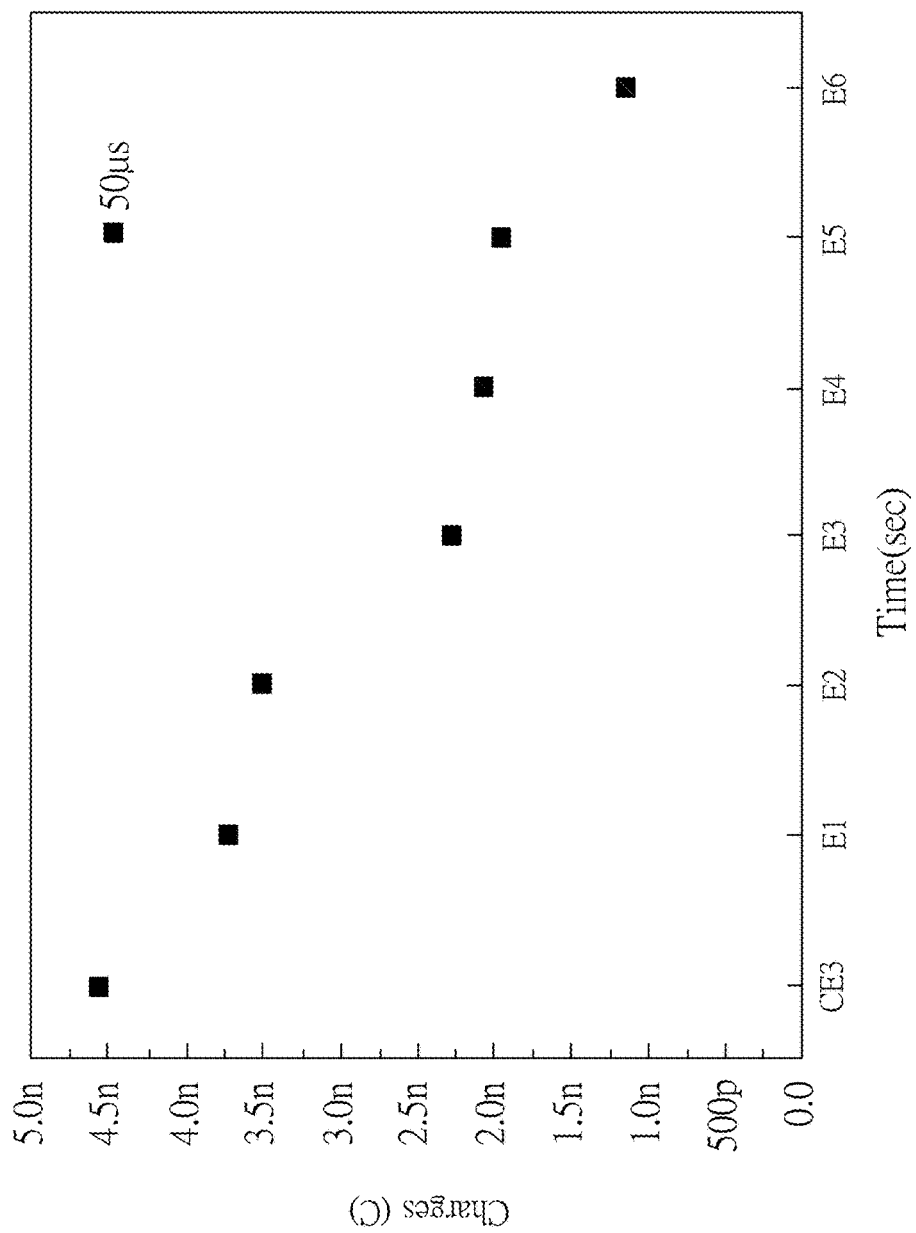
FIG. 9 shows the accumulated charges of Examples 1 to 6 and Comparative Example 3 at 50 µs after the application of the voltage pulse with respect to the analyte concentration in a logarithmic scale.
Figure 10:
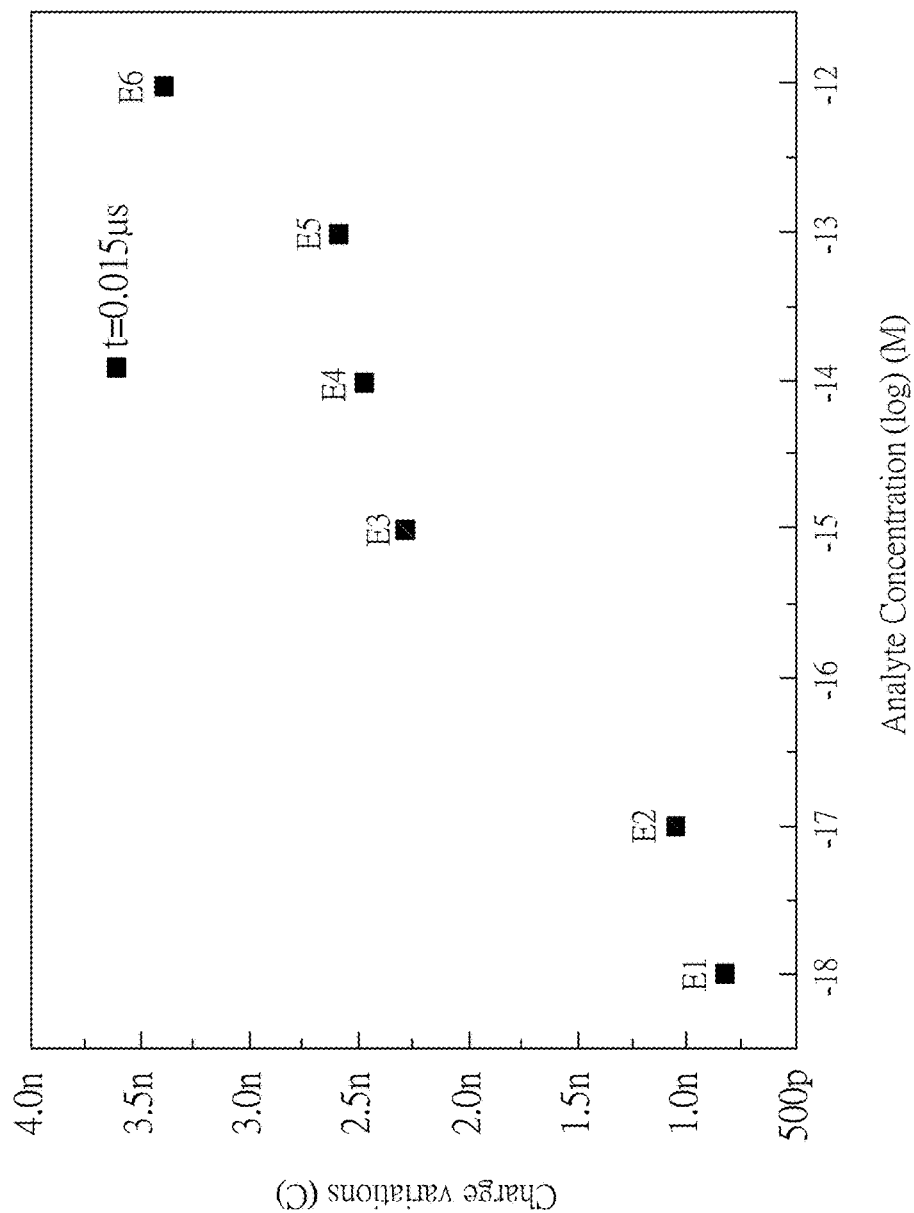
FIG. 10 shows the charge variations between each of Examples 1 to 6 and Comparative Example 3 at 0.015 µs after the application of the voltage pulse with respect to the analyte concentration in a logarithmic scale.
Figure 14:
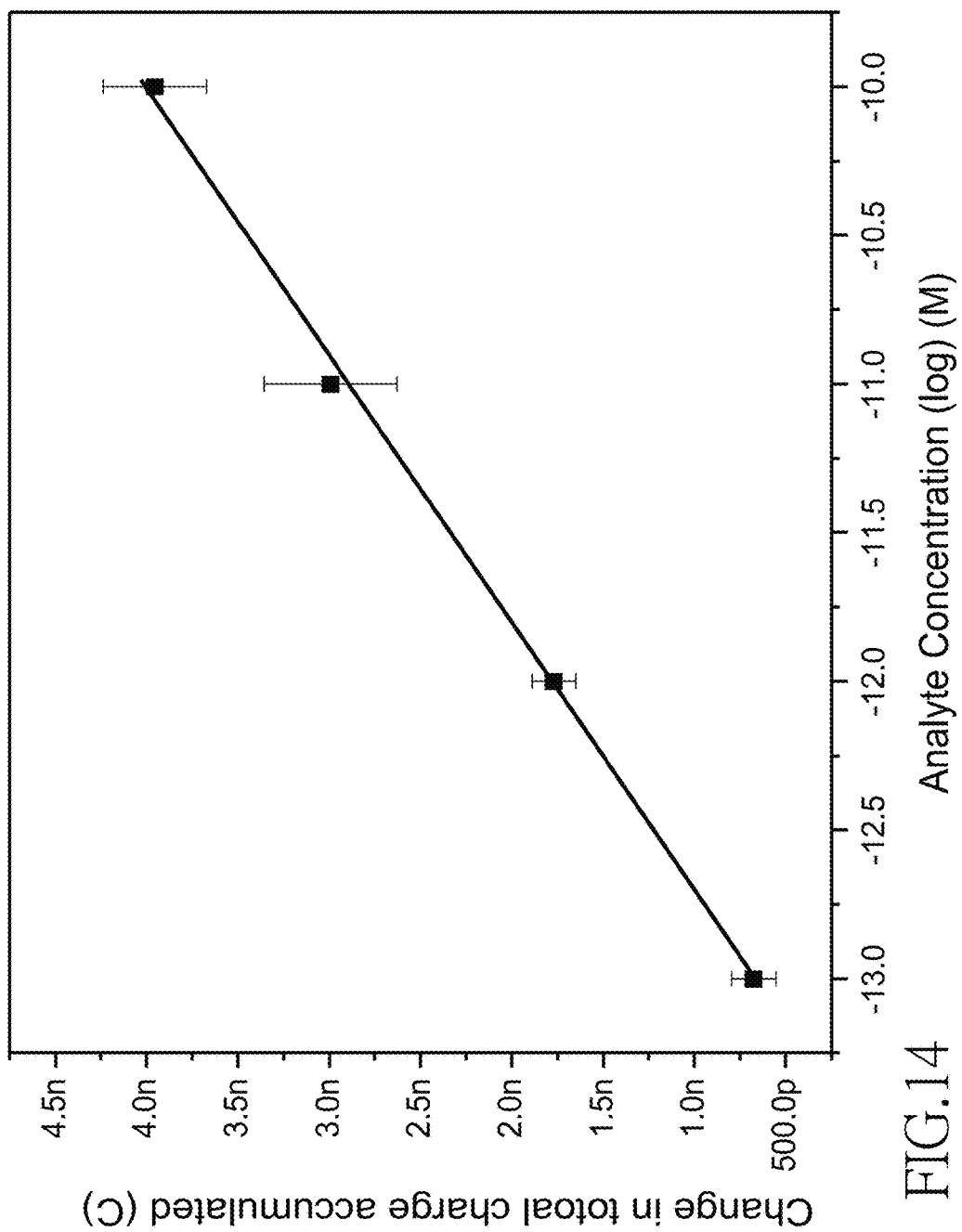
FIG. 14 shows the change in accumulated total charges obtained after subtracting the reference response current from the monitored response currents of Examples 7 to 10 at 50 µs after the application of the voltage pulse with respect to the analyte concentration in a logarithmic scale.

Integration computational processing on the response currents of Examples 1 to 6, Examples 7 to 10, Comparative Examples 1 to 3 and Comparative Examples 4 to 6 with respect to the pulse width was performed by the analyzer (Agilent B1530A) to obtain the amount of total charges accumulated at the biosensor, as illustrated in FIGS. 8 to 9 and 13. Similar to the response currents, it is shown that the amount of total charges accumulated at the biosensor is correlated to the analyte concentration in the liquid sample. As shown in FIG. 9, which illustrates the total charges of Examples 1 to 6 and Comparative Example 3 accumulated at the biosensor at 50 µs after the application of the voltage pulse, the total accumulated charges of Examples 1 to 6 are approximately in inverse proportion to the HIV-1 RT protein concentration in the liquid sample. In addition, FIG. 10 further shows the accumulated charge variations between each of Examples 1 to 6 and Comparative Example 3, where the total accumulated charges of the Examples were subtracted by the charges attributed to the reference response current. The charge variations of Examples 1 to 6 are also approximately in proportion to the logarithmic analyte concentration in the liquid sample. Similarly, FIG. 14 illustrates the accumulated charge variations between each of Examples 7 to 10 and Comparative Example 6 at 50 µs after the application of the voltage pulse and shows the same relationship as depicted by FIG. 10. As such, the charges accumulated at the biosensor within a pulse width of an applied voltage pulse can be another reliable analyzing factor.

Figure 11:
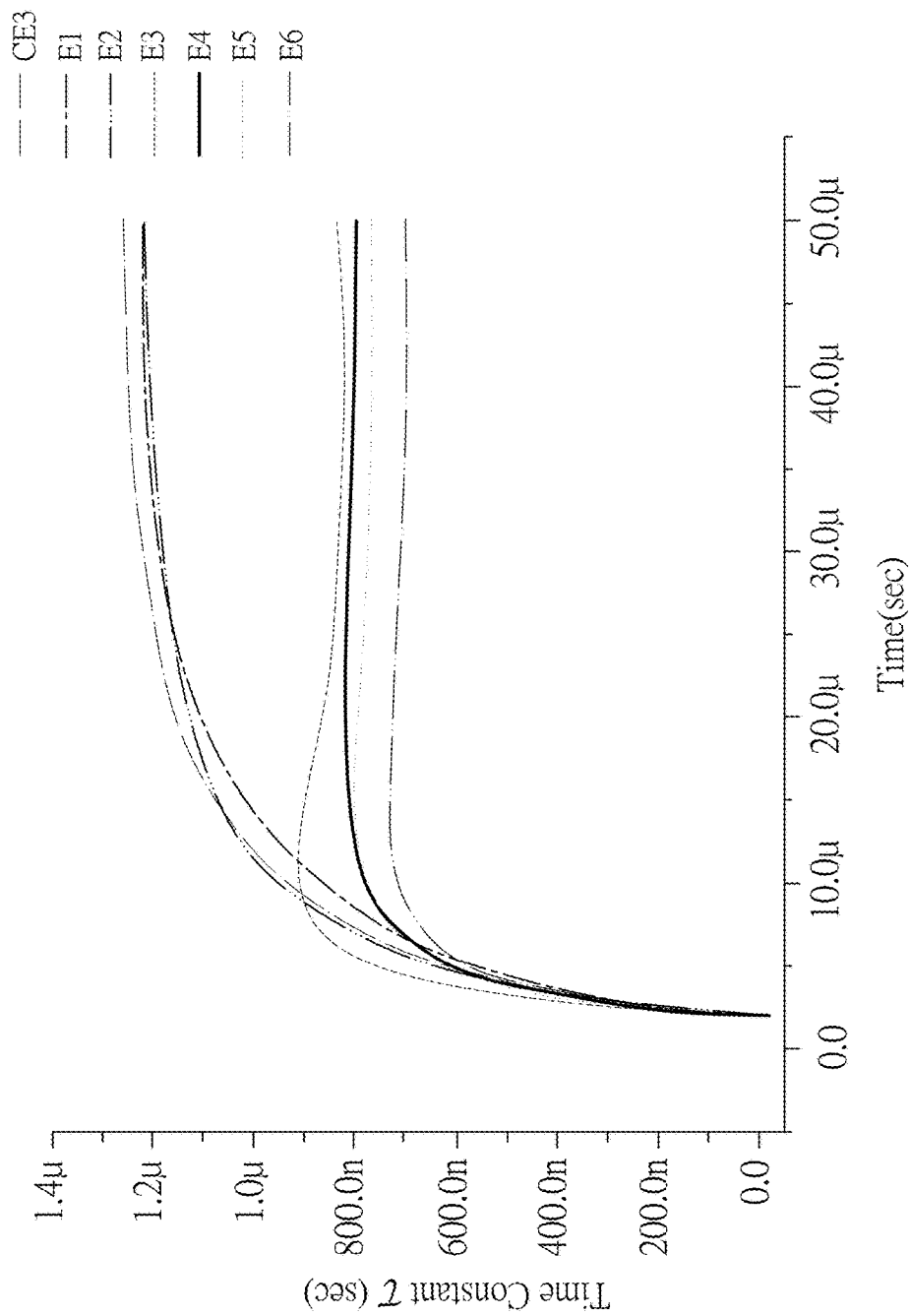
FIG. 11 shows time constants of Examples 1 to 6 and Comparative Example 3 with respect to the voltage pulse applying time.
Figure 12:
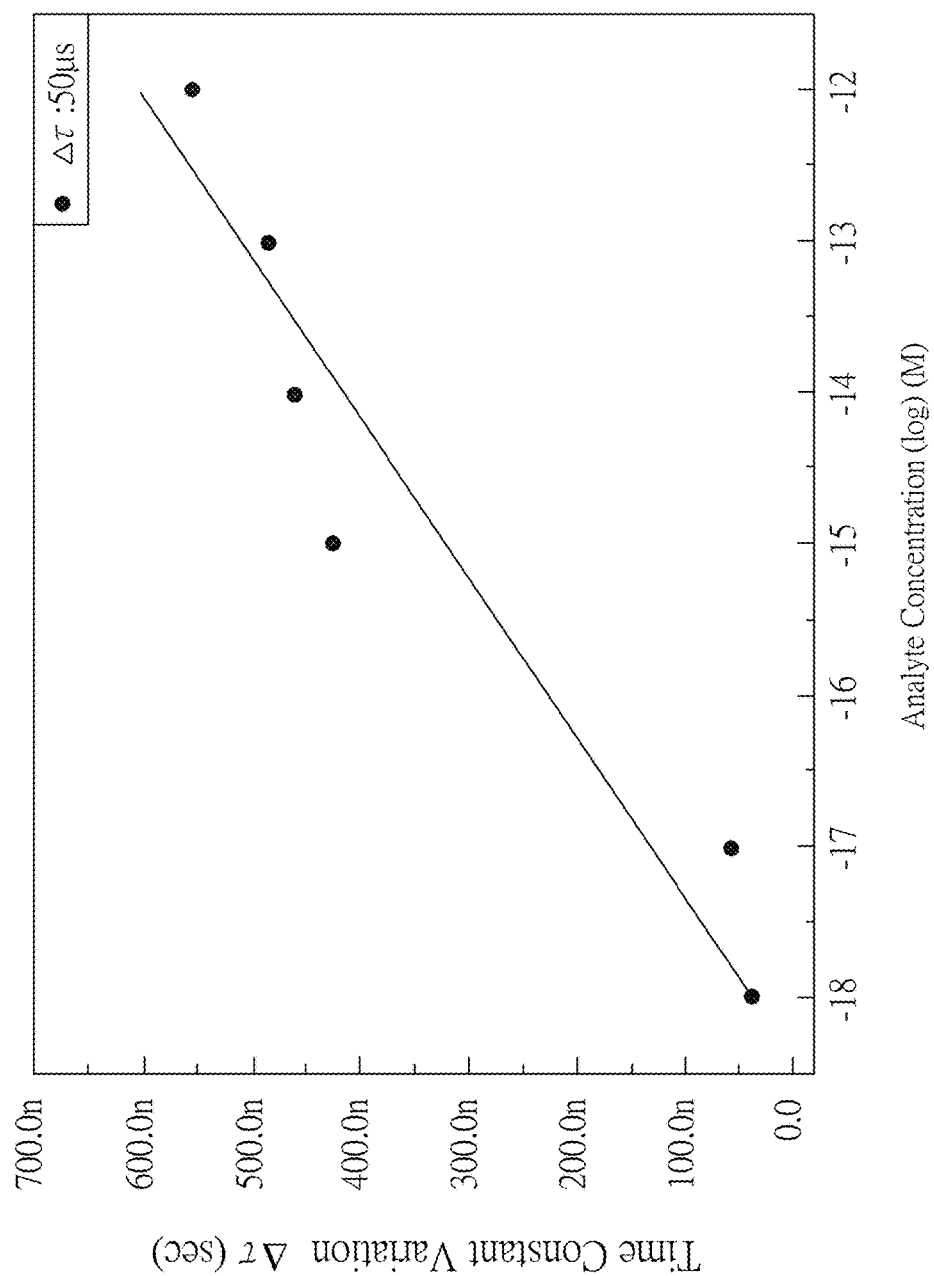
FIG. 12 shows time constant variations between each of Examples 1 to 6 and Comparative Example 3 at 50 µs after the application of the voltage pulse with respect to the analyte concentration in a logarithmic scale.

Arithmetic computational processing to divide entries of the response current of each of Examples 1 to 6 and Comparative Example 3 by a maximum value of the monitored response current, and integration computational processing on results of the arithmetic computational processing with respect to the pulse width (up to 50 µs) of the applied voltage pulse were performed to obtain a time constant ($\tau$) for each of Examples 1 to 6 and Comparative Example 3 as depicted in FIG. 11. FIG. 12 further shows that the time constant variations between each of Examples 1 to 6 and Comparative Example 3 are also in proportion to the logarithmic analyte concentration in the liquid sample. Similar to the response current and the accumulated charges, it is evident that the time constant can be utilized as yet another reliable analyzing factor for analyzing analyte concentration in a liquid sample utilizing the biosensor of the present disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for analyzing concentration of an analyte in a liquid sample, comprising:
    applying the liquid sample to a biosensor, wherein the biosensor includes a transistor that has a drain, a source and a gate surface disposed between the drain and the source, and a reactive electrode spaced apart from the gate surface of the transistor, the reactive electrode having a receptor immobilized thereon for specific binding with the analyte in the liquid sample and being configured to, together with the gate surface of the transistor, contact the liquid sample;
    applying a voltage pulse between the reactive electrode and the source of the transistor, the voltage pulse having a pulse width;
    monitoring a response current, which is produced in response to the voltage pulse, within the pulse width from the biosensor;
    performing arithmetic computational processing to divide entries of the response current by a maximum value of the response current;
    performing integration computational processing on results of the arithmetic computational processing with respect to at least a certain period in the pulse width to obtain time constant; and
    analyzing the time constant that is correlated to the concentration of the analyte in the liquid sample.

2. The method of claim 1, wherein the pulse width of the voltage pulse is not greater than $10^{-3}$ second.

3. The method of claim 1, wherein the transistor is selected from the group consisting of a high electron mobility transistor (HEMT), a silicon-based transistor, a nanowire transistor, a graphene transistor, and a molybdenum disulfide ($MoS_2$)-included transistor.

4. The method of claim 1, wherein the reactive electrode has a surface layer that has the receptor immobilized thereon and that contains gold.

5. The method of claim 1, wherein the reactive electrode is disposed on top of and faces the gate surface of the transistor.

6. The method of claim 1, wherein the reactive electrode and the gate surface of the transistor are arranged in a coplanar manner.

7. The method of claim 1, further comprising steps of:
    prior to the application of the liquid sample, applying a reference protein solution to the biosensor;
    applying the voltage pulse between the reactive electrode and the source of the transistor after applying the reference protein solution;

monitoring a reference response current within the pulse width from the source of the biosensor; and removing the reference protein solution.

8. The method of claim 5, further comprising a step of performing subtraction processing on the response current with respect to the pulse width by subtracting out the reference response current.

\* \* \* \* \*